(12) United States Patent
Grandt

(10) Patent No.: US 9,572,961 B2
(45) Date of Patent: Feb. 21, 2017

(54) MEDICAL BALLOON FOR A CATHETER

(71) Applicant: ABBOTT LABORATORIES VASCULAR ENTERPRISES LIMITED, Dublin (IE)

(72) Inventor: Axel Grandt, Strassberg (DE)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 120 days.

(21) Appl. No.: 14/573,875

(22) Filed: Dec. 17, 2014

(65) Prior Publication Data

US 2015/0174382 A1 Jun. 25, 2015

(30) Foreign Application Priority Data

Dec. 20, 2013 (EP) .................................. 13198915

(51) Int. Cl.
*A61M 29/00* (2006.01)
*A61M 25/10* (2013.01)
*A61F 2/958* (2013.01)

(52) U.S. Cl.
CPC .......... *A61M 25/1025* (2013.01); *A61F 2/958* (2013.01); *A61M 25/1002* (2013.01); *A61M 25/1034* (2013.01); *A61F 2220/005* (2013.01); *A61F 2220/0058* (2013.01); *A61M 25/104* (2013.01); *A61M 2025/1059* (2013.01); *Y10T 156/1005* (2015.01)

(58) Field of Classification Search
CPC .................... A61M 25/1034; A61M 25/1002; A61M 25/10; A61M 25/1025; A61M 29/00; A61F 2220/0058; A61F 2/958
See application file for complete search history.

(56) References Cited

U.S. PATENT DOCUMENTS 5,454,788 A * 10/1995 Walker .................... A61L 29/04
604/103
2012/0035704 A1 * 2/2012 Grandt .................... A61F 2/958
623/1.12

* cited by examiner

*Primary Examiner* — Victor Nguyen
(74) *Attorney, Agent, or Firm* — Workman Nydegger; John Kwok

(57) ABSTRACT

A medical balloon for deployment of stents is disclosed. The medical balloon includes a central section; a proximal and a distal cone section; a proximal and a distal shaft section; a proximal sleeve which is arranged coaxial to and radially inside the proximal shaft section. The proximal end of the proximal shaft section is permanently connected and/or unitarily formed with the proximal end of the proximal sleeve, and distal thereto, at least part of the proximal cone section is connected with the proximal sleeve by an adhesive bond, and a distal sleeve which is arranged coaxial to and radially inside the distal shaft section. Methods of manufacturing a medical balloon are disclosed.

18 Claims, 7 Drawing Sheets

MEDICAL BALLOON FOR A CATHETER

CROSS REFERENCE TO RELATED APPLICATIONS

This application claims priority to European Patent Application No. 13198915.4, filed on Dec. 20, 2013, the entirety of which is incorporated herein by reference.

The invention relates to a medical balloon for a catheter, a catheter having such a balloon and a method for manufacturing such a balloon.

BACKGROUND OF THE INVENTION

In medicine, a natural conduit in a body may be locally flow constricted or damaged. A stent or stent graft may be inserted into this natural conduit, in order to counteract such a flow constriction or to repair damage. Stents may be deployed by means of a balloon catheter. The stent is crimped around the balloon before deployment, the catheter is introduced into a body lumen and once the balloon is positioned appropriately, the balloon is inflated and expands the stent.

FIGS. 1a to 1d illustrate a few exemplary chronologic steps of inflating a balloon from the state of the art. The balloon shown in these Figures is used for deploying a stent which is crimped around the balloon. FIG. 1a shows the unexpanded state of the balloon and stent. As shown in FIG. 1b, when starting to introduce pressure into the balloon, its expansion begins at the outer ends. This phenomena is called dog boning and is caused by the resistance for expanding this part being smaller than in the center of the balloon/stent assembly (the struts in the middle are held in position from both sides, whereas at the end struts are only held from one side). From there, the expansion of the balloon/stent proceeds towards a center of the balloon/stent until the entire balloon is expanded, as shown in FIG. 1d. The dog-boning of the balloon cones has a so-called foreshortening effect for the stent, which means that the stent is shortened longitudinally to a small extend. This foreshortening effect is undesirable, because it makes the expanded length deviate from the unexpanded length.

FIG. 2 schematically shows a typical diagram of the relationship between the pressure inside a balloon and its diameter. As illustrated, the pressure inside the balloon increases up to a nominal pressure 1, at which the balloon is considered to be fully expanded. If the pressure is increased further, the balloon diameter does not increase substantially any more. When exceeding a burst pressure 2, the balloon may burst.

SUMMARY OF THE INVENTION

It is an object of the present invention to provide a balloon having improved expansion properties.

This object is solved with a balloon and method for manufacturing the same according to the independent claims. Advantageous further developments are subject of the dependent claims.

According to an embodiment of the invention there is provided a medical balloon for deployment of stents, comprising a central section; a proximal and a distal cone section; a proximal and a distal shaft section; a proximal sleeve which is arranged coaxial to and radially inside the proximal shaft section, wherein the proximal end of the proximal shaft section is permanently connected and/or unitarily formed with the proximal end of the proximal sleeve, and distal thereto (distal to the permanent connection and/or unitary forming), at least part of the proximal cone section is connected with the proximal sleeve by an adhesive bond, and a distal sleeve which is arranged coaxial to and radially inside the distal shaft section, wherein the distal end of the distal shaft section is permanently connected and/or unitarily formed with the distal end of the distal sleeve, and proximal thereto (proximal to the permanent connection and/or unitary forming), at least part of the distal cone section is connected with the distal sleeve by an adhesive bond. The term "permanently connected" is defined as a connection which does not detach during normal use for which the device is constructed. In particular, the connection is maintained at least up to a rated burst pressure of the balloon. The term "unitarily formed" is defined as being continuously formed, in particular from the same material, in particular monolithically formed. This embodiment has the advantage that the foreshortening of stent deployed by the balloon can be reduced. This leads to more reliable and predictable stenting result.

According to another embodiment of the invention, the balloon requires a higher inflation pressure radially around the adhesive bonds than in a center of the balloon.

According to another embodiment of the invention, the adhesive bonds are adapted such that an inflation pressure for releasing the adhesively bonded parts of the proximal and distal cone sections from the respective proximal and distal sleeves is higher than an inflation pressure at which a center of the balloon starts expanding.

According to a yet further embodiment of the invention, the adhesive bonds are adapted such that the adhesively bonded parts of the proximal and distal cone sections release from the respective sleeves at an inflation pressure which is lower than a rated balloon burst pressure. The "rated balloon burst pressure" is defined as the maximum statistically guaranteed pressure to which a balloon can be inflated without failing. In particular, it is defined as the pressure at which the balloon has 95% confidence that 99.9% of the balloons will not burst at or below upon single inflation. The value is commonly indicated by the producer of a catheter or balloon and depends among other from the material the balloon is made of. According to this embodiment the balloon is prevented from damage.

According to a yet further embodiment of the invention, the adhesive bonds are adapted such that the adhesively bonded parts of the proximal and distal cone sections release from the respective sleeves at an inflation pressure which is higher than an inflation pressure at which a center of the balloon is substantially fully expanded. The term "fully expanded" is indicating the state in which the center of the balloon (the middle of the balloon in the longitudinal direction) reaches its labeled diameter which is the intended expanded diameter, the balloon is designed for.

According to a further embodiment of the invention, the proximal sleeve is formed by folding a proximal portion of the proximal shaft portion inwards, and the distal sleeve is formed by folding a distal portion of the distal shaft portion inwards. This means that in during manufacturing, a proximal portion of the proximal shaft portion and a distal portion of the distal shaft portion becomes a sleeve, respectively, (and is referred to as "sleeve" after folding). In order to do so, the shaft portions of the tubing for manufacturing the balloon have to be much longer compared to the manufacturing method in which separate sleeves are provided (tubing is a cylindrical raw material for producing balloons). This embodiment with inwardly folded sleeves avoids manufacturing of a separate sleeve.

According to a yet further embodiment of the invention, the permanent connection between the sleeves and the shaft portions are formed by welding, respectively. This embodiment allows adapting the design precisely to user requirements by designing the sleeves more independently from the shaft sections, e.g. by using different materials.

According to a further embodiment of the invention, shaft portions comprise an opening for injecting the adhesive, respectively.

Further, the invention provides a catheter having a medical balloon according to one of the preceding embodiments.

Moreover, the invention provides methods for manufacturing such a medical balloon. These methods comprise the same advantages as the embodiments of the medical balloon described above.

According to a further embodiment of the invention, there is provided a method of manufacturing a medical balloon, comprising the steps of providing a balloon tubing having a central section, a proximal and distal cone section, and a proximal and distal shaft section; folding the two longitudinal ends of the proximal and distal shaft sections inwards to form two sleeves coaxial to and radially inside the shaft sections; inserting adhesive to a position longitudinally inwards of the two folds and in between at least part of each cone section and the sleeves.

According to a another embodiment of the invention, there is provided a method of manufacturing a medical balloon, comprising the steps of providing a balloon tubing having a central section, a proximal and distal cone section, and a proximal and distal shaft section; providing a proximal and a distal sleeve and arranging them coaxial to the proximal and distal shaft sections, respectively; welding the proximal end of the proximal shaft section to the proximal end of the proximal sleeve, and the distal end of the distal shaft section to the distal end of the distal sleeve; inserting adhesive to a position longitudinally inwards of the two folds and in between at least part of each cone section and the sleeves.

Yet another embodiment of the invention, further comprises, before the injecting adhesive step, the step of folding the cone sections and the central section into a contracted delivery configuration.

These and other embodiments are described in more detail with reference to the Figures.

DETAILED DESCRIPTION OF EXEMPLARY EMBODIMENTS OF THE INVENTION

Figure 3:
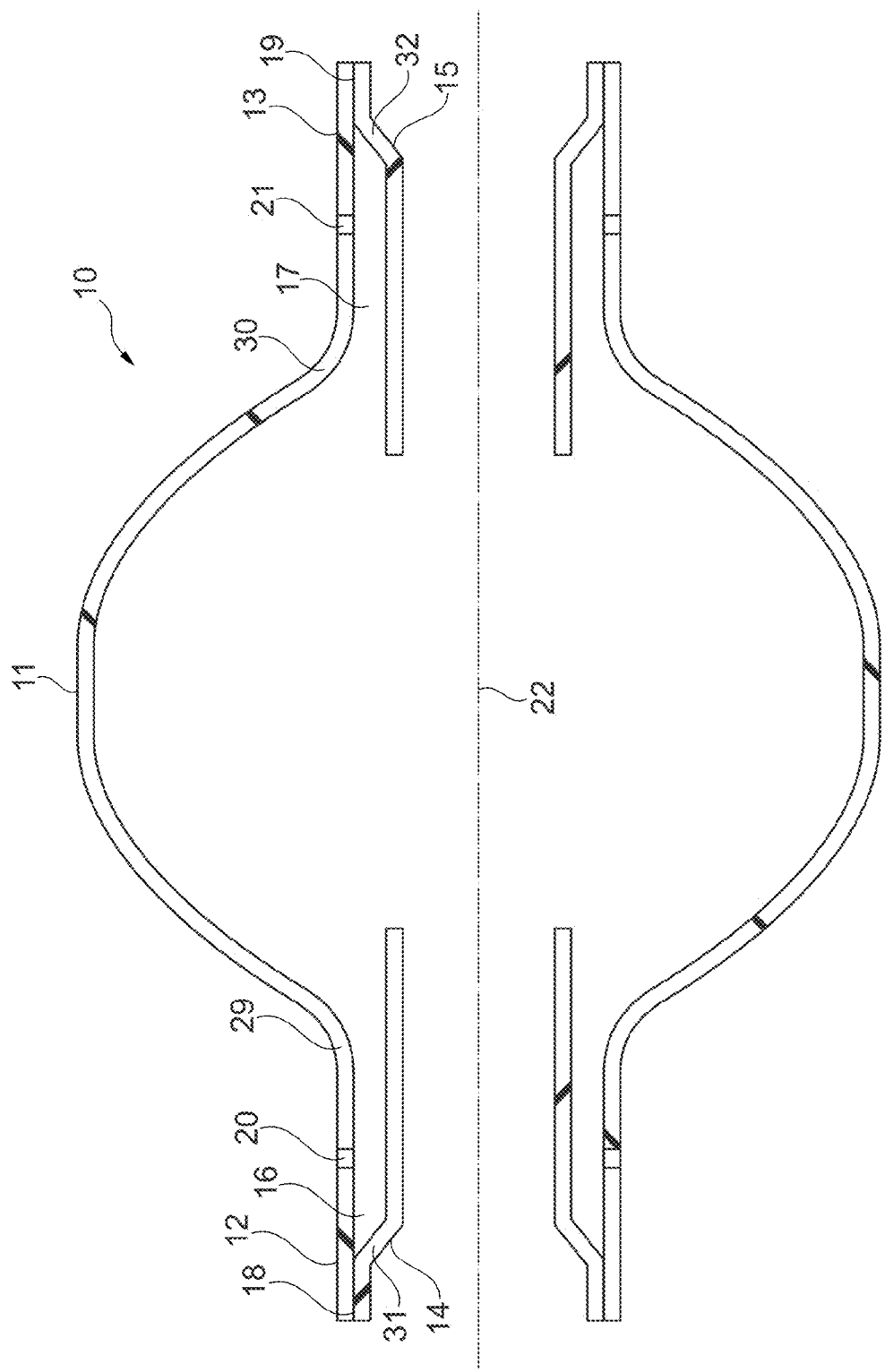
FIG. 3 schematically illustrates a balloon according to an embodiment of the invention.
Figure 4:
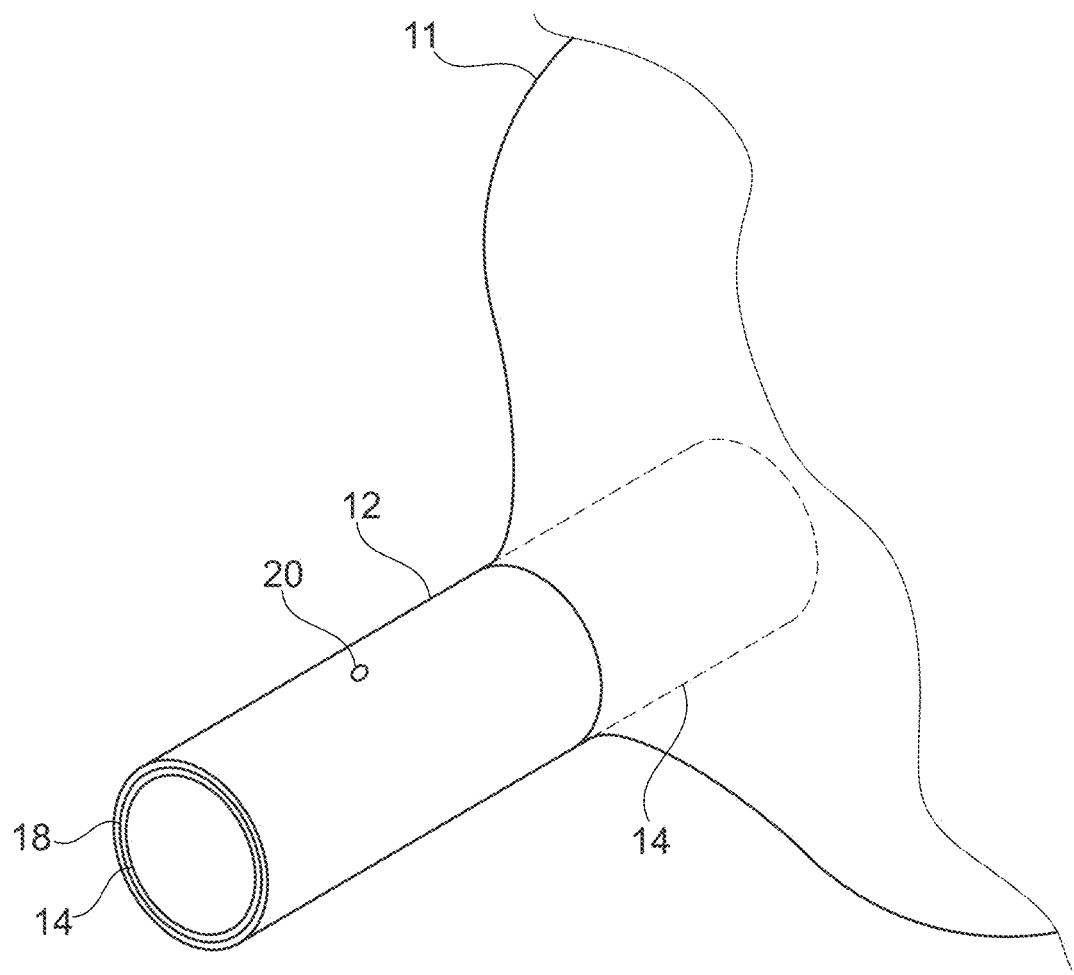
FIG. 4 schematically illustrates a three-dimensional view of one side of the balloon of FIG. 3.
Figure 5:
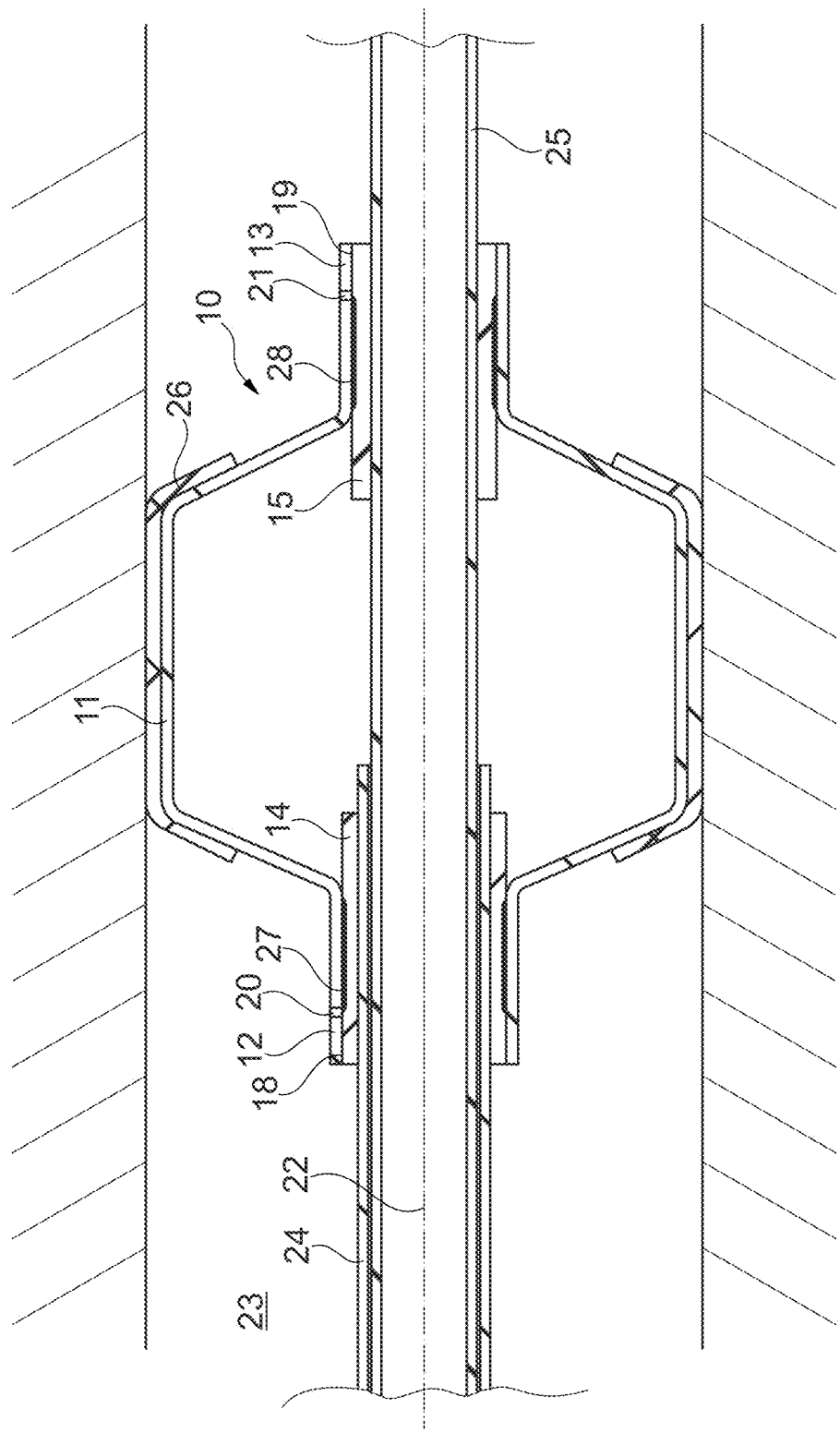
FIG. 5 schematically illustrates an expansion of the balloon of FIG. 3 in a state in which the adhesive bond is still attached, and FIG. 6 schematically illustrates an expansion of the balloon after the state shown in FIG. 5, in which the adhesive bond is detached.
Figure 6:
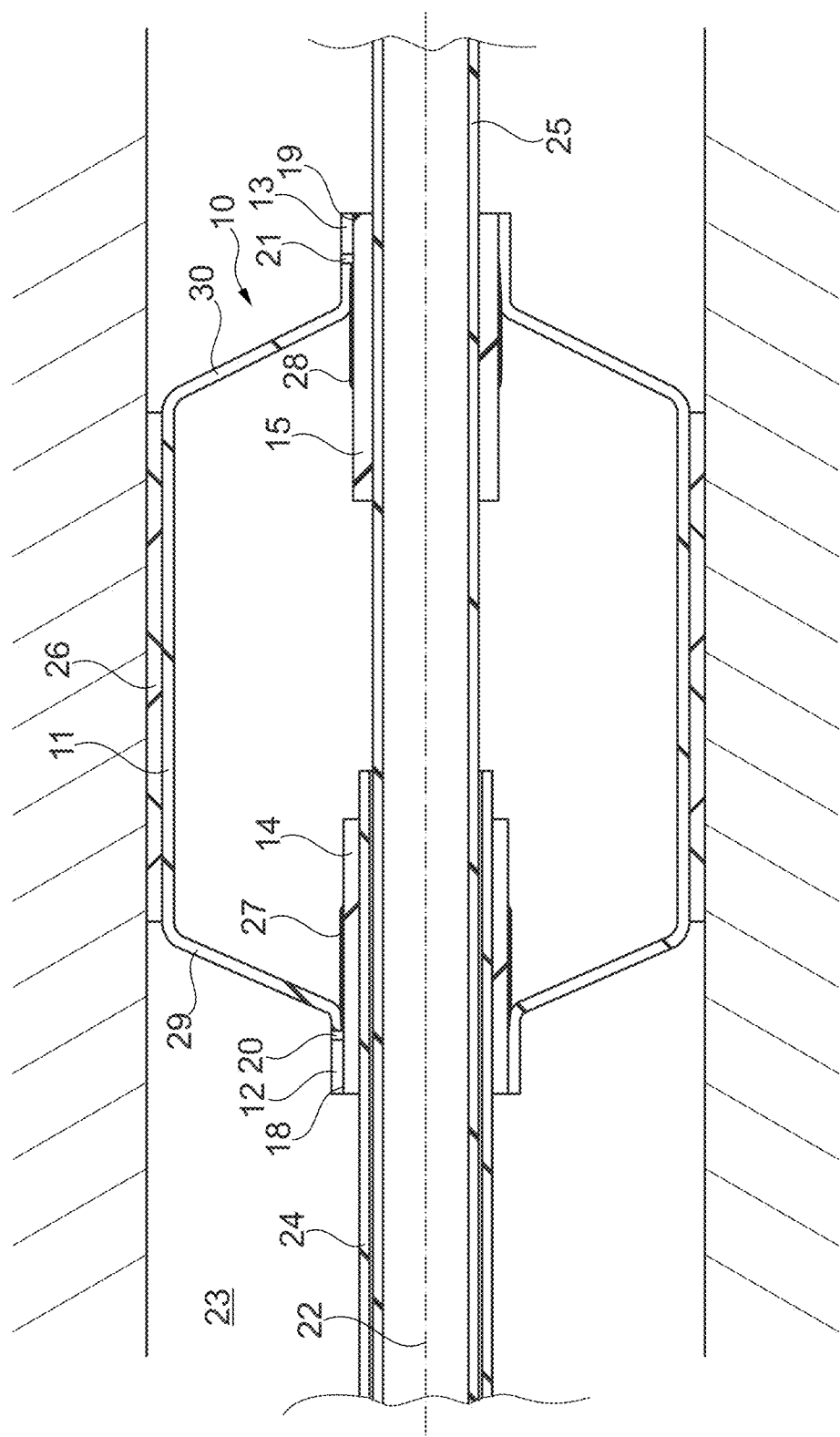

FIG. 3 schematically illustrates a medical balloon 10 (or simply referred to as "balloon") according to an exemplary embodiment of the invention. FIG. 4 schematically illustrates part of the balloon 10 in a three-dimensional view. The balloon 10 can be formed in numeral different shapes, such as a conical balloon, a spherical balloon, a long spherical balloon, an offset balloon, a square balloon, a tapered balloon, a stepped balloon, etc. FIG. 3 illustrates as one example a balloon 10 having a central section 11 which is cylindrical shaped in a fully expanded state (shown in FIG. 6). The portions of the balloon 10 at both longitudinal ends of the central section 11, are a proximal cone section 29 and a distal cone section 30, both of which have a cone shape in the fully expanded state of the balloon, which state is illustrated in FIG. 6. The terms "proximal" and "distal" are well known in connection with catheters, wherein "distal" refers to the end of the catheter which is inserted first into a patient and "proximal" is the opposite end at which usually the actuating elements of the catheter are located. The proximal end portion of the balloon 10 is referred to as proximal shaft section 12, and the distal end portion as distal shaft section 13. In a non-expanded delivery configuration, the balloon 10 is folded to a basically cylindrical configuration and a stent which is to be deployed by the balloon catheter is crimped around the folded balloon. Coaxial to the proximal shaft section 12, the balloon 10 comprises a proximal sleeve 14 and coaxial to the distal shaft section 13 a distal sleeve 15. The sleeves 14, 15 are arranged coaxial to and radially inside the respective shaft sections 12, 13, however, the sleeves are longer than the shaft sections, in particular the sleeves 12, 13 are arranged over the entire length of the shaft sections 12, 13 and along the remaining length of the sleeves 14, 15 they are surrounded by the proximal and distal cone sections 29, 30 respectively, which cone sections 29, 30 are also basically cylindrical in a non-expanded configuration of the balloon 10. The purpose of the sleeves 14, 15 is to form a proximal and distal adhesive pocket 16, 17 in between the sleeves 14, 15 and the respective surrounding cone sections 29, 30. These adhesive pockets 16, 17 are filled with adhesive such that the portions of the balloon, which are attached by adhesive, form reinforced portions which have the effect that the balloon is no longer inflated beginning from the outer ends towards the center of the balloon 10, but vice versa, namely from the center towards the outer ends of the balloon 10. This way, the foreshortening effect can be reduced. This effect according to the invention is illustrated in FIGS. 5 and 6, wherein FIG. 5 shows the state before the adhesive bond breaks or peels off, and FIG. 6 shows a state after the adhesive bond broke or peeled off.

In the following, the balloon 10 according to this embodiment is described in more detail. In order to distinguish the states shown in FIGS. 5 and 6, the state illustrated in FIG. 5 is called the "partly expanded state before adhesive bond release", and the state shown in FIG. 6 is called the "fully expanded state".

The shaft sections 12 and 13 are adapted to surround and contact a shaft of a catheter, with the sleeves 14 and 15 arranged in between. The sleeves 14 and 15 can be provided in different ways. One possibility is to fold the outer end portions of the shaft sections inwards. This way the proximal sleeve 14 is unitarily formed with the proximal shaft section 12, and the distal sleeve 15 is unitarily formed with the distal shaft section 13. Additionally, the fold may be welded such that additionally permanent connections 18 and 19 are formed between outer ends of the shaft sections 12, 13 and the outer ends of the sleeves 14, 15, respectively. Another option is to provide two separate sleeves 14 and 15 (as shown in FIG. 3) which are welded to the shaft sections 12, 13, in order to form the permanent connections 18, 19. In more detail, the proximal end of the proximal shaft section 12 is welded to the proximal end of the proximal sleeve 14, and the distal end of the distal shaft section 13 is welded to the distal end of the distal sleeve 15. Alternatively to welding, the permanent connections 18, 19 could be formed by glue, which forms a much stronger bond as the adhesive in the adhesive pockets 16, 17, it would have to even withstand a rated burst pressure inside the balloon 10. This glue is different from the one in the adhesive pockets 18, 19 and (in order to avoid confusion) the term "adhesive" in this description always refers to the adhesive in the adhesive pockets 16, 17. In particular, the permanent connection 18, 19 (e.g. welding) is formed between the sleeves 14, 15 and the associated shaft sections 12, 13, over the entire length of the shaft sections 12, 13, which entire length is in FIG. 3 for example the length over which the shaft sections 12, 13 are illustrated as directly contacting the associated sleeves 14, 15.

In order to be able to fill the adhesive pockets 16, 17 with adhesive, openings 20, 21 may be provided, e.g. one or more for each adhesive pocket 16, 17. The openings 20, 21 may be provided through the walls of the proximal and distal shaft sections 12, 13, as shown in FIGS. 3 to 6. In more detail, the opening 20 is provided distal to the permanent connection 18 and proximal to the proximal cone section 29, whereas the opening 21 is provided proximal to the permanent connection 19 and distal to the distal cone section 30. Alternatively, the openings may be provided through the sleeves 14, 15 directly longitudinally inwards from the permanent connections 18, 19, as indicated by reference numerals 31 and 32 in FIG. 3. As a further alternative, the adhesive may be injected with a needle inserted along the longitudinal direction of the balloon in between the shaft section and the sleeve, namely the needle goes through the permanent connection 18, 19, wherein the permanent connection is sealed thereafter, or the permanent connection 18, 19 is established after the adhesive is inserted. Alternatively, the openings 20, 21 can be omitted and the adhesive is directly applied onto the sleeves 14, 15 or the corresponding area on the inside of the cone sections 29, 30, before the sleeves 14, 15 are folded inwards (in case of unitarily formed sleeves) or inserted (in case of separate sleeves). Or, instead of liquid or viscous adhesive, adhesive tape may be used which is attached before the sleeves 14, 15 are folded inwards or inserted. Or as a further alternative, when injecting the adhesive by means of a needle, the openings 20, 21 can be omitted or do not have to be provided in advance, because the needle simply penetrates the respective walls on the way to the adhesive pockets 16, 17. It is possible to use adhesive band aid, tacky adhesive, UV adhesive, etc.

FIG. 5 schematically illustrates an expansion of the balloon of FIG. 3 in a state in which the adhesive bond is still attached (in this description called partly expanded state before adhesive bond release), and FIG. 6 schematically illustrates an expansion of the balloon after the state shown in FIG. 5, in which the adhesive bond is already detached (in this description called fully expanded state). These Figures show the balloon 10 attached to the catheter only part of which is illustrated, and arranged within a body lumen 23 of a human or animal body. The body lumen 23 may be in particular a vein or artery. The proximal sleeve 14 may be directly in contact with and attached to an outer tubular member 24 of the catheter, and the distal sleeve 15 may be directly in contact with and attached to an inner tubular member 25 of the catheter. Between inner and outer tubular member 24, 25, a lumen may be formed for introducing air, gas or fluid from a proximal end of the catheter into the balloon 10 in order to inflate it. When inflating the balloon 10, a stent 26 which is crimped around the non-inflated balloon 10, is expanded together with the balloon 10 and pressed against the wall of the body lumen 23. For deflating the balloon 10, the inflation medium is extracted the opposite direction as for inflating, wherein the stent 26 remains in the expanded configuration, as well known from the state of the art.

In the partly expanded state before adhesive bond release, adhesive 27 introduced into the adhesive pocket 16 is provided adjacent and distal to the proximal permanent connection 18, and bonding at least part of the proximal cone section 29 (i.e. at least part of its length) and (part of) the proximal sleeve 14. Equivalently, adhesive 28 introduced into the adhesive pocket 17 is provided adjacent and proximal to the distal permanent connection 19, and bonding the at least part of the distal cone section 30 (i.e. at least part of its length) and (part of) the distal sleeve 15. The openings 20 and 21 are much smaller in reality than illustrated in the Figures. In particular, the adhesive could be injected by using a needle such that the openings may have the diameter of a needle penetration. After injecting adhesive the openings 20, 21 may be sealed with the same adhesive as the injected one, or a stronger one. FIGS. 5 and 6 show the openings 20, 21 in a sealed state.

Figure 1A:
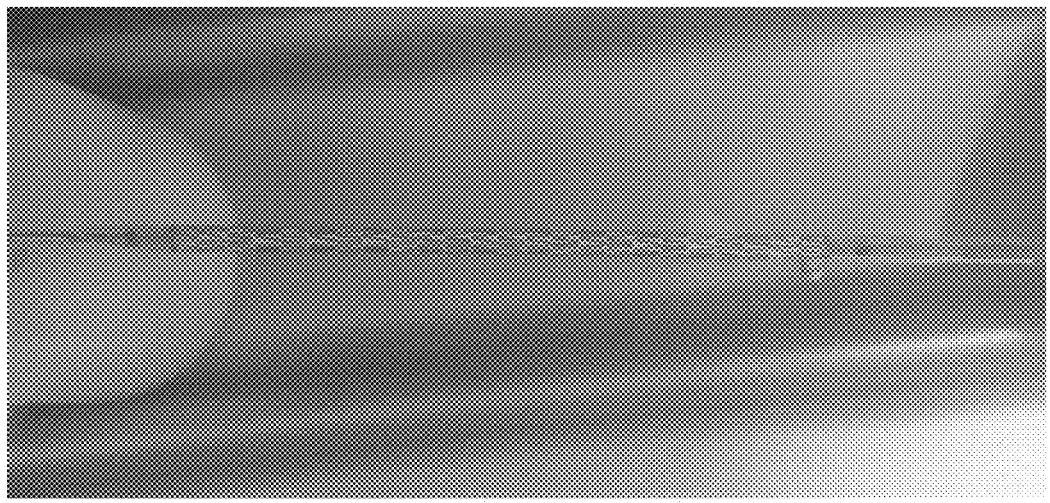
FIGS. 1a to 1d illustrate different chronologic steps of inflating a balloon from the state of the art.
Figure 1B:
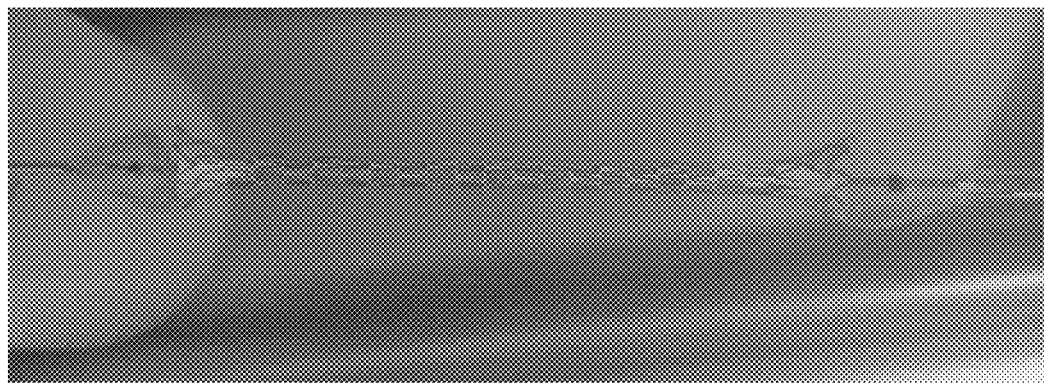
Figure 1C:
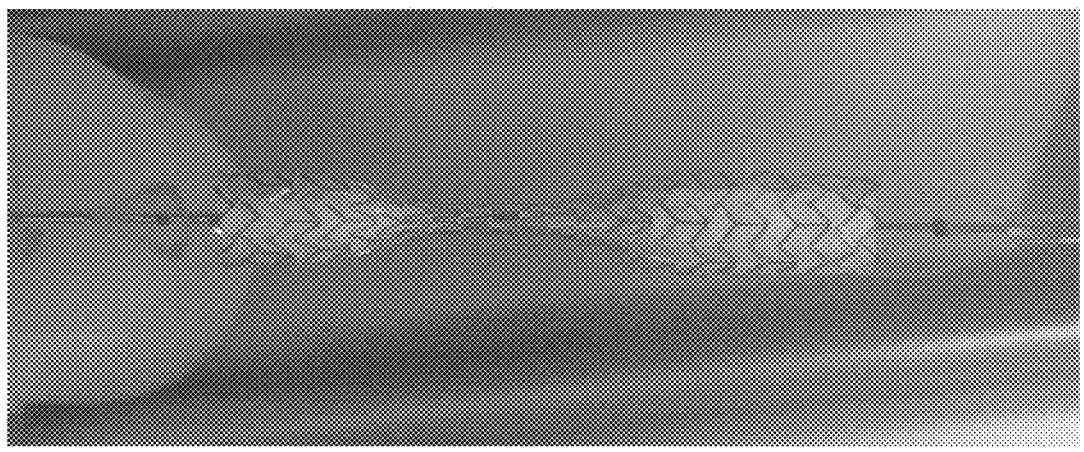
Figure 1D:
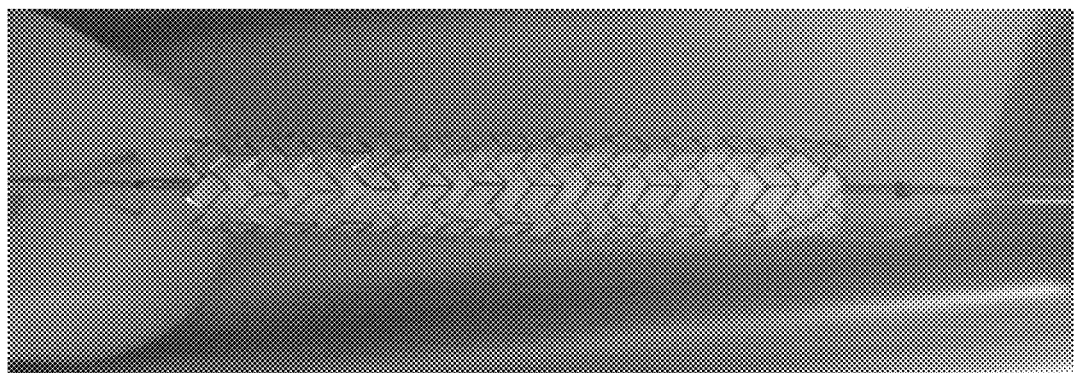
Figure 2:
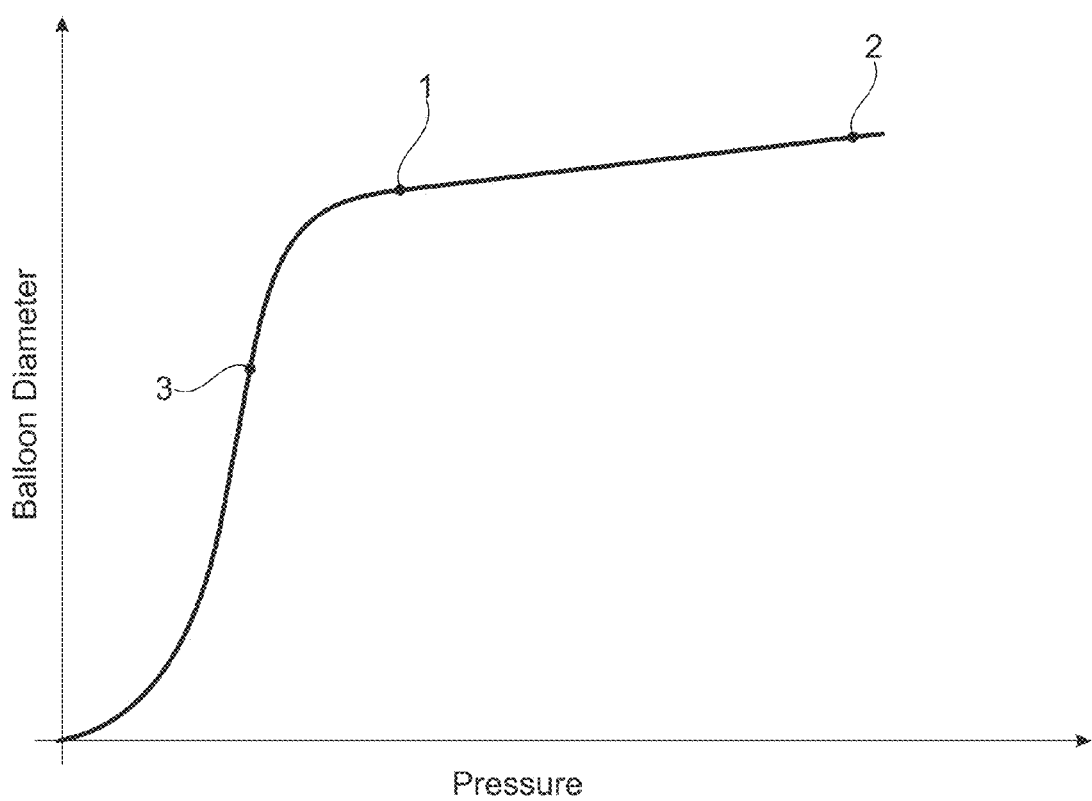
FIG. 2 schematically shows a typical diagram of an inflation pressure inside a balloon versus its diameter.

As already described, due to the bond formed by the adhesive 27, 28, a higher pressure is required to inflate the parts of the cone sections 29, 30 which are bonded to the respective sleeves 14, 15. Therefore, the balloon 11 will start inflating substantially from the center (the middle in a longitudinal direction along the centerline 22) towards its longitudinal ends. Analogously, the stent 26 is expanded from its center towards its ends. In the partly expanded state before adhesive bond release, most of the stent 26 is expanded. During a normal inflation of a balloon, the internal balloon pressure is increasing, as already illustrated in connection with FIG. 2. Thus, in the partly expanded state before adhesive bond release, the pressure is higher than in an initial phase of the balloon inflation. According to the chosen adhesive and the amount of used adhesive 27, 28, the adhesive bond breaks or detaches and the cone sections 29, 30 detach from the sleeves 14, 15 with the permanent connections 18, 19 maintained. This way, the remaining inner volume of the balloon 10 is inflated and the rest of the stent 26 is expanded as shown in FIG. 6. The pressure inside the balloon 10 at which the adhesive bond 27, 28 is designed to detach, is in particular lower than the rated burst pressure 2 of the balloon 10, in order to avoid damage of the balloon 10. Further, the pressure is preferably higher than an initial pressure at which the center of the balloon 10 starts to expand. In particularly, the pressure may be higher than the pressure at which the center of the balloon 10 is fully expanded, which may be around point 3 in FIG. 2. In particular, the inner balloon pressure at which the adhesive bond 27, 28 breaks may be in a pressure range from half of the nominal balloon pressure 1 (see FIG. 2) and 150% of the nominal balloon pressure 1. The nominal balloon pressure 1 would be the pressure at which the balloon 1 is fully expanded as shown in FIG. 6. This would be a practical range which is high enough to start inflating from the center and low enough to avoid damage of the balloon 10. Normally, during inflation, the inner balloon pressure is increased by increasing the introduced pressure. However, the invention would also be realizable if the inflation is conducted by just opening a valve such that a constant pressure is introduced into the balloon 10, because also in this case, constant pressure introduced from outside would lead to an increasing pressure inside the balloon until reaching the value of the introduced constant pressure.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously.

The invention claimed is:

1. A medical balloon for deployment of stents, comprising
a central section;
a proximal and a distal cone section;
a proximal and a distal shaft section;
a proximal sleeve which is arranged coaxial to and radially inside the proximal shaft section, wherein a proximal end of the proximal shaft section is permanently connected and/or unitarily formed with a proximal end of the proximal sleeve, and distal thereto, at least part of the proximal cone section is connected with the proximal sleeve by an adhesive bond; and
a distal sleeve which is arranged coaxial to and radially inside the distal shaft section, wherein a distal end of the distal shaft section is permanently connected and/or unitarily formed with a distal end of the distal sleeve, and proximal thereto, at least part of the distal cone section is connected with the distal sleeve by an adhesive bond,
wherein, the adhesive bonds are adapted such that an inflation pressure for releasing the adhesively bonded parts of the proximal and distal cone sections from the respective proximal and distal sleeves is higher than an inflation pressure at which a center of the balloon starts expanding.

2. The medical balloon according to claim 1, wherein the balloon requires a higher inflation pressure radially around the adhesive bonds than in a center of the balloon.

3. The medical balloon according to claim 1, wherein the adhesive bonds are adapted such that the adhesively bonded parts of the proximal and distal cone sections release from the respective sleeves at an inflation pressure which is lower than a rated balloon burst pressure.

4. The medical balloon according to claim 1, wherein the adhesive bonds are adapted such that the adhesively bonded parts of the proximal and distal cone sections release from the respective sleeves at an inflation pressure which is higher than an inflation pressure at which a center of the balloon is substantially fully expanded.

5. The medical balloon according to claim 1, wherein the proximal sleeve is formed by folding a proximal portion of the proximal shaft section inwards, and the distal sleeve is formed by folding a distal portion of the distal shaft portion inwards.

6. The medical balloon according to claim 1, wherein the permanent connection between the sleeves and the shaft sections are formed by welding, respectively.

7. The medical balloon according to claim 1, wherein shaft portions comprise an opening for injecting the adhesive, respectively.

8. The medical balloon according to claim 1, wherein the medical balloon forms part of a catheter.

9. A medical balloon for deployment of stents, comprising
a central section;
a proximal and a distal cone section;
a proximal and a distal shaft section;
a proximal sleeve which is arranged coaxial to and radially inside the proximal shaft section, wherein a proximal end of the proximal shaft section is permanently connected and/or unitarily formed with a proximal end of the proximal sleeve, and distal thereto, at least part of the proximal cone section is connected with the proximal sleeve by an adhesive bond; and
a distal sleeve which is arranged coaxial to and radially inside the distal shaft section, wherein a distal end of the distal shaft section is permanently connected and/or unitarily formed with a distal end of the distal sleeve, and proximal thereto, at least part of the distal cone section is connected with the distal sleeve by an adhesive bond,
wherein the adhesive bonds are adapted such that the adhesively bonded parts of the proximal and distal cone sections release from the respective sleeves at an inflation pressure which is higher than an inflation pressure at which a center of the balloon is substantially fully expanded.

10. The medical balloon according to claim 9, wherein the balloon requires a higher inflation pressure radially around the adhesive bonds than in a center of the balloon.

11. The medical balloon according to claim 9, wherein the proximal sleeve is formed by folding a proximal portion of the proximal shaft section inwards, and the distal sleeve is formed by folding a distal portion of the distal shaft portion inwards.

12. The medical balloon according to claim 9, wherein the permanent connection between the sleeves and the shaft sections are formed by welding, respectively.

13. The medical balloon according to claim 9, wherein shaft portions comprise an opening for injecting the adhesive, respectively.

14. A medical balloon for deployment of stents, comprising
a central section;
a proximal and a distal cone section;
a proximal and a distal shaft section;
a proximal sleeve which is arranged coaxial to and radially inside the proximal shaft section, wherein a proximal end of the proximal shaft section is permanently connected and/or unitarily formed with a proximal end of the proximal sleeve, and distal thereto, at least part of the proximal cone section is connected with the proximal sleeve by an adhesive bond; and
a distal sleeve which is arranged coaxial to and radially inside the distal shaft section, wherein a distal end of the distal shaft section is permanently connected and/or unitarily formed with a distal end of the distal sleeve, and proximal thereto, at least part of the distal cone section is connected with the distal sleeve by an adhesive bond,
wherein shaft portions comprise an opening for injecting the adhesive, respectively.

15. The medical balloon according to claim 14, wherein the balloon requires a higher inflation pressure radially around the adhesive bonds than in a center of the balloon.

16. The medical balloon according to claim 14, wherein the proximal sleeve is formed by folding a proximal portion of the proximal shaft section inwards, and the distal sleeve is formed by folding a distal portion of the distal shaft portion inwards.

17. The medical balloon according to claim 14, wherein the permanent connection between the sleeves and the shaft sections are formed by welding, respectively.

18. The medical balloon according to claim 14, wherein shaft portions comprise an opening for injecting the adhesive, respectively.

\* \* \* \* \*